US009949748B2

(12) United States Patent
Taylor et al.

(10) Patent No.: US 9,949,748 B2
(45) Date of Patent: Apr. 24, 2018

(54) LAPAROSCOPIC TISSUE RETRIEVAL SYSTEM

(71) Applicant: Applied Medical Resources Corporation, Rancho Santa Margarita, CA (US)

(72) Inventors: Scott V. Taylor, Rancho Santa Margarita, CA (US); Henry Kahle, Corona, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 258 days.

(21) Appl. No.: 14/623,265

(22) Filed: Feb. 16, 2015

(65) Prior Publication Data

US 2015/0157304 A1 Jun. 11, 2015

Related U.S. Application Data

(63) Continuation of application No. 13/252,110, filed on Oct. 3, 2011, now Pat. No. 8,956,370.

(Continued)

(51) Int. Cl.

*A61B 17/221* (2006.01)
*A61B 17/00* (2006.01)

(52) U.S. Cl.

CPC ...... *A61B 17/221* (2013.01); *A61B 17/00234* (2013.01); *A61B 2017/00287* (2013.01); *A61B 2017/00292* (2013.01)

(58) Field of Classification Search

CPC ........ A61B 17/221; A61B 2017/00287; A61B 2017/2212; A61B 2017/00358; A61B 17/32056

See application file for complete search history.

(56) References Cited

U.S. PATENT DOCUMENTS 30,471 A 10/1860 Dudley
1,609,014 A 11/1926 Dowd (Continued)

FOREIGN PATENT DOCUMENTS

DE 25796 1/1884
DE 4216165 11/1992

(Continued)

OTHER PUBLICATIONS

The International Bureau of WIPO, The International Preliminary Report on Patentability for International Application No. PCT/US2006/060007 dated Apr. 24, 2008.

(Continued)

*Primary Examiner* — Thomas McEvoy
(74) *Attorney, Agent, or Firm* — John F. Heal

(57) ABSTRACT

A tissue retrieval system can contain and withdraw excised tissue specimens from within a body cavity. The tissue retrieval system can include a tissue retrieval bag, a foldable actuator, and an introducer. The foldable actuator can be foldable between an insertion configuration for placement through an access device without the aid of a grasper or applicator, and a deployed configuration for supporting the tissue retrieval bag in an open state. The actuator can have a foldable handle to facilitate withdrawal from the body cavity. After insertion of the tissue specimens into the retrieval bag, the retrieval bag is then cinched closed to prevent spillage of its contents and to prevent contamination of the body cavity and body cavity wall during withdrawal of the retrieval bag from within the body cavity.

15 Claims, 6 Drawing Sheets

10
44
20
80
82
84
37
54
38
10
52
82
84
20

Related U.S. Application Data

(60) Provisional application No. 61/389,107, filed on Oct. 1, 2010.

(56) References Cited

U.S. PATENT DOCUMENTS 3,476,114 A 11/1969 Shannon et al.
3,476,115 A 11/1969 Graeff et al.
4,287,807 A 9/1981 Pacharis et al.
4,428,375 A 1/1984 Ellman
4,732,150 A 3/1988 Keener, Jr.
4,741,335 A 5/1988 Okada
4,991,593 A 2/1991 Levahn
5,037,379 A 8/1991 Clayman et al.
5,074,867 A 12/1991 Wilk
5,143,082 A 9/1992 Kindberg et al.
5,147,371 A 9/1992 Washington et al.
5,176,687 A 1/1993 Hasson et al.
5,190,542 A 3/1993 Nakao et al.
5,190,555 A 3/1993 Wetter et al.
5,190,561 A 3/1993 Graber
5,192,284 A 3/1993 Pleatman
5,192,286 A 3/1993 Phan et al.
5,195,507 A 3/1993 Bilweis
5,201,740 A 4/1993 Nakao et al.
5,215,521 A 6/1993 Cochran et al.
5,234,439 A 8/1993 Wilk et al.
5,279,539 A 1/1994 Bohan et al.
5,279,548 A 1/1994 Essig et al.
5,308,327 A 5/1994 Heaven et al.
5,312,416 A 5/1994 Spaeth et al.
5,336,227 A 8/1994 Nakao et al.
5,337,754 A 8/1994 Heaven et al.
5,341,815 A 8/1994 Cofone et al.
5,352,184 A 10/1994 Goldberg et al.
5,354,303 A 10/1994 Spaeth et al.
5,366,460 A 11/1994 Eberbach
5,368,597 A 11/1994 Pagedas
5,417,684 A 5/1995 Jackson et al.
5,417,697 A 5/1995 Wilk et al.
5,465,731 A 11/1995 Bell et al.
5,480,404 A 1/1996 Kammerer et al.
5,486,182 A 1/1996 Nakao et al.
5,486,183 A 1/1996 Middleman et al.
RE35,164 E 3/1996 Kindberg et al.
5,509,923 A 4/1996 Middleman et al.
5,524,633 A 6/1996 Heaven et al.
5,535,759 A 7/1996 Wilk
5,601,572 A 2/1997 Middleman et al.
5,611,803 A 3/1997 Heaven et al.
5,613,973 A 3/1997 Jackson et al.
5,632,746 A 5/1997 Middleman et al.
5,643,283 A 7/1997 Younker
5,647,372 A 7/1997 Tovey et al.
5,655,657 A 8/1997 Roshdy
5,656,012 A 8/1997 Sienkiewicz
5,679,423 A 10/1997 Shah
5,681,324 A 10/1997 Kammerer et al.
5,720,754 A 2/1998 Middleman et al.
5,735,289 A 4/1998 Pfeffer et al.
5,741,271 A 4/1998 Nakao et al.
5,749,879 A 5/1998 Middleman et al.
5,759,187 A 6/1998 Nakao et al.
5,779,716 A 7/1998 Cano et al.
5,782,839 A 7/1998 Hart et al.
5,785,677 A 7/1998 Auweiler
5,788,709 A 8/1998 Riek et al.
5,809,621 A 9/1998 McCree et al.
5,820,628 A 10/1998 Middleman et al.
5,836,953 A 11/1998 Yoon
5,853,374 A 12/1998 Hart et al.
5,904,690 A 5/1999 Middleman et al.
5,947,978 A 9/1999 Holsinger
5,971,995 A 10/1999 Rousseau
5,980,544 A 11/1999 Vaitekunas
5,997,547 A 12/1999 Nakao et al.
6,004,330 A 12/1999 Middleman et al.
6,015,415 A 1/2000 Avellanet
6,019,770 A 2/2000 Christoudias
6,059,793 A 5/2000 Pagedas
6,206,889 B1 3/2001 Bennardo
6,228,095 B1 5/2001 Dennis
6,258,102 B1 7/2001 Pagedas
6,264,663 B1 7/2001 Cano
6,350,267 B1 2/2002 Stefanchik
6,383,197 B1 5/2002 Conlon et al.
6,387,102 B2 5/2002 Pagedas
6,406,440 B1 6/2002 Stefanchik
6,409,733 B1 6/2002 Conlon et al.
6,419,639 B2 7/2002 Walther et al.
6,447,523 B1 9/2002 Middleman et al.
6,575,988 B2 6/2003 Rousseau
6,805,699 B2 10/2004 Shimm
6,814,739 B2 11/2004 Secrest et al.
6,958,069 B2 10/2005 Shipp et al.
6,986,774 B2 1/2006 Middleman et al.
7,041,055 B2 5/2006 Young et al.
7,115,125 B2 10/2006 Nakao
7,270,663 B2 9/2007 Nakao
7,547,310 B2 6/2009 Whitfield
7,618,437 B2 11/2009 Nakao
7,670,346 B2 3/2010 Whitfield
8,062,306 B2 11/2011 Nobis et al.
2003/0100919 A1 5/2003 Hopkins et al.
2004/0087969 A1 5/2004 Kayan
2004/0097960 A1 5/2004 Terachi et al.
2004/0138587 A1 7/2004 Lyons
2004/0158280 A1 8/2004 Morris et al.
2004/0254573 A1 12/2004 Dycus et al.
2005/0119668 A1* 6/2005 Teague ................. A61B 17/221 606/127
2005/0165411 A1 7/2005 Orban
2005/0267489 A1 12/2005 Secrest et al.
2005/0267492 A1 12/2005 Poncet et al.
2006/0052799 A1 3/2006 Middleman et al.
2006/0229639 A1 3/2006 Whitfield
2006/0173468 A1 8/2006 Simmon et al.
2006/0200169 A1 9/2006 Sniffin
2006/0200170 A1 9/2006 Aranyi
2006/0276805 A1 12/2006 Yu
2007/0088370 A1 4/2007 Kahle et al.
2008/0033451 A1 2/2008 Rieber et al.
2008/0221587 A1 9/2008 Schwartz
2008/0221588 A1 9/2008 Hollis et al.
2008/0234696 A1 9/2008 Taylor et al.
2009/0043315 A1 2/2009 Moon
2009/0082779 A1 3/2009 Nakao
2009/0192510 A1 7/2009 Bahney
2009/0306683 A1 12/2009 Zwolinski et al.
2010/0076451 A1 3/2010 Zwolinski et al.
2010/0152609 A1 6/2010 Zwolinski et al.
2010/0152746 A1 6/2010 Ceniccola et al.
2012/0029526 A1* 2/2012 Hewitt ............. A61B 17/00234 606/113

FOREIGN PATENT DOCUMENTS

DE 197 07 361 8/1998
EP 499243 8/1992
EP 0 947 166 10/1999
JP 5-115493 5/1993
JP 6-154161 6/1994
SU 1537229 1/1990
WO WO 1993/15671 8/1993
WO WO 1993/24063 12/1993
WO WO 1994/13215 6/1994
WO WO 2003/105674 12/2003
WO WO 2007/081601 7/2007

OTHER PUBLICATIONS

The International Bureau of WIPO, The International Preliminary Report on Patentability for International Application No. PCT/US2006/060022, dated Jul. 24, 2008.

(56) References Cited

OTHER PUBLICATIONS

European Patent Office, International Search Report and Written Opinion of the International Searching Authority for International Application No. PCT/US2006/060007 dated Mar. 2, 2007.
European Patent Office, International Search Report and Written Opinion of the International Searching Authority for International Application No. PCT/US2006/060022 dated Jun. 5, 2007.
United States Surgical, Tyco Healthcare Group LP, Autosuture ENDO CATCH Single-Use Specimen Pouch, Frequently Asked Questions and Features and Benefits (web pages), 2004, 4 pages.
United States Surgical, Tyco Healthcare Group LP, Autosuture ENDOCATCH Gold 10 mm Single-Use Specimen Pouch, 10000-25912, Product Information Data Sheet, Feb. 2004, 2 pages.
United States Surgical, Tyco Healthcare Group LP, Autosuture ENDOCATCH II Single-Use Specimen Pouch, 10000-19724, Product Information Data Sheet, Aug. 2002, 2 pages.
Conmed Corporation, EndoSurgery Products, Hand Held Laparoscopic Instruments, Product Descriptions (Web pages), 2004, 3 pages.
Cook Group Inc., Cook Urological, Cook® Drainage Pouch Sets, Product Description (Web page), 2003, 1 page.
Johnson & Johnson Gateway LLC, Ethicon Endo-Surgery Inc., Endoscopic Product Family, Endopouch Retriever Specimen Retrieval Bag, Product Description (Web Page), 2000-2005, 1 page.
U.S. Pat. No. 5,853,374, filed Oct. 11, 1995 entitled Tissue Retrieval System and associated file history (now abandoned).
U.S. Appl. No. 11/549,971, filed Oct. 16, 2006 entitled Tissue Retrieval System and associated file history.
U.S. Appl. No. 12/902,055, filed Oct. 11, 2010 entitled "Single Incision Laparoscopic Tissue Retrieval System" and associated file history.
U.S. Appl. No. 11/549,701, filed Oct. 16, 2006, entitled "Device for Isolating and Removing Tissue From a Body Cavity" and associated file history.
International Search Report and Written Opinion for International Application No. PCT/US2010/052190, dated Feb. 3, 2011.
The International Bureau of WIPO, International Preliminary Report on Patentability, for International Application No. PCT/US2010/052190, entitled "Single Incision Laparoscopic Tissue Retrieval System", dated Apr. 11, 2012.
International Searching Authority, The International Search Report and Written Opinion for International Application No. PCT/US2011/054647,entitled Laparoscopic Tissue Retrieval System, dated Feb. 21, 2012.
International Searching Authority, International Preliminary Report on Patentability for International Application No. PCT/US2011/054647, entitled "Laparoscopic Tissue Retrieval System", dated Apr. 16, 2013.

* cited by examiner

LAPAROSCOPIC TISSUE RETRIEVAL SYSTEM

CROSS REFERENCE TO RELATED APPLICATIONS

This application is a continuation of U.S. patent application Ser. No. 13/252,110, entitled LAPAROSCOPIC TISSUE RETRIEVAL SYSTEM, filed Oct. 3, 2011, currently pending, which claims the benefit of U.S. Provisional Patent Application Ser. No. 61/389,107, entitled LAPAROSCOPIC TISSUE RETRIEVAL SYSTEM, filed Oct. 1, 2010, the entireties of which are each hereby incorporated herein by reference.

BACKGROUND OF THE INVENTION

Field of the Invention

The present application relates generally to apparatuses and methods for capturing and retrieving tissue from body cavities and in particular to a specimen retrieval system including a tissue retrieval bag device.

Description of the Related Art

Laparoscopic surgery is typically performed through trocars, which provide access across the abdominal wall and into the abdominal cavity. In some of surgeries, tissue disposed within the abdominal cavity is cut and removed from the body. However, removal of such tissue from the body may prove difficult due to the limited confines inherent with laparoscopic surgery and the available laparoscopic surgical instruments. For example, to reduce the invasiveness to a patient, it can be desirable to introduce all of the surgical instruments through a single laparoscopic port having a relatively small size. Also, removed tissue may include an infected or cancerous mass or organ, as well as blood, bile and other liquids, all referred to herein as tissue, which may pose infection issues or other complications if left within the body.

Prior art retrieval bags have been provided without introducer tubes and require the use of a grasper to introduce the retrieval bag into the body cavity. The prior art retrieval bags are typically grasped with a grasper in the cuff portion of the retrieval bag and then pushed through the trocar. If resistance is encountered during advancement of the retrieval bag through the trocar, it is possible to tear the retrieval bag. Also, the jaw configurations of laparoscopic graspers vary tremendously from manufacturer to manufacturer. Some laparoscopic grasper jaws include padding to provide for an atraumatic grip while other laparoscopic grasper jaws include teeth which can be traumatic. The diameters of the jaws and shafts of laparoscopic graspers can also vary from manufacturer to manufacturer. Larger diameter graspers can increase the force required to insert prior art retrieval bags through trocars increasing the potential for the retrieval bag to tear during advancement through a trocar.

It is desirable to grasp, capture, retain and enclose this tissue while in the body cavity, and then remove the enclosed tissue through the trocar or incision. Containment of the tissue as quickly as possible with minimal disturbance to the surgical site is also desirable. A generally compact and single unit device would also prove desirable as devices generally bulky and complicated have several shortcomings and lack optimal efficiency in particular with the limited space in operating rooms and access ports in the body cavity.

SUMMARY OF THE INVENTION

In certain embodiments, a tissue retrieval system is provided herein. The tissue retrieval system comprises: a tissue retrieval pouch, an actuator, and an introducer. The tissue retrieval pouch has an open end, a closed end opposite the open end, and a cuff extending peripherally around the open end. The actuator has a first end, a second end opposite the first end. The actuator comprises: a generally cylindrical segment; a hoop segment; and a flexible section. The generally cylindrical segment is between the first end and the second end. The cylindrical segment defines a longitudinal axis of the actuator. The hoop segment extends from the generally cylindrical segment to the second end of the actuator. At least a portion of the hoop segment is positioned within the cuff of the tissue retrieval pouch. The flexible section is between the first end and the second end such that the actuator is foldable at the flexible section about an axis transverse to the longitudinal axis. The actuator is foldable between a first configuration in which the hoop segment extends distally from the generally cylindrical segment and a second configuration in which the hoop segment extends proximally from the generally cylindrical segment. The introducer comprises a tubular introducer member. The tubular introducer member has a first end, a second end opposite the first end, and a lumen extending therebetween. The actuator is slidably disposed in the lumen of the introducer such that at least a portion of the hoop segment extends from the second end of the introducer.

In certain embodiments, a tissue retrieval system is provided. The tissue retrieval system comprises: a tissue retrieval bag; and a foldable actuator. The tissue retrieval bag has an open end, a closed end, and a cuff extending peripherally around at least a portion of the open end. The foldable actuator has a first end and a second end opposite the first end. The actuator comprises: an elongate arm and a hoop segment. The elongate arm is between the first end and the second end. The elongate arm defines a longitudinal axis of the actuator. The hoop segment extends from the elongate arm to the second end. The hoop segment is biased into an open state. The hoop segment is disposed within the cuff of the tissue retrieval bag. The hoop segment is foldable about an axis transverse to the longitudinal axis such that in a folded state the hoop segment and the tissue retrieval bag extend from the elongate arm in a first direction towards the first end, and in an unfolded state, the hoop segment and the tissue retrieval bag extend from the elongate arm in a second direction opposite the first direction away from the first end.

In certain embodiments, a tissue retrieval system comprises a tissue retrieval pouch, an actuator, and an introducer. The tissue retrieval pouch has an open end, a closed end opposite the open end, and a cuff extending peripherally around the open end. The actuator has a first end, a second end opposite the first end and comprises a generally cylindrical segment and a hoop segment. The generally cylindrical segment is between the first end and the second end. The cylindrical segment defines a longitudinal axis of the actuator. The hoop segment extends from the generally cylindrical segment to the second end of the actuator. At least a portion of the hoop segment is positioned within the cuff of the tissue retrieval pouch. The introducer comprises a tubular introducer member having a first end, a second end opposite the first end, and a lumen extending therebetween. A portion of the tissue retrieval pouch is coupled to the second end of the introducer. The actuator is slidably disposed in the lumen of the introducer and slidable between an open position in which in which a majority of the hoop segment of the actuator is positioned outside the introducer and the open end of the tissue retrieval pouch is in an open state and a second position in which a majority of the hoop segment is withdrawn into the lumen of the introducer and the open end of the tissue retrieval bag is in a cinched state.

In certain embodiments, a method of retrieving tissue is provided. The method comprises: folding a tissue retrieval system into an insertion configuration; and inserting the tissue retrieval system in the insertion configuration through a surgical access site into a surgical field. The tissue retrieval system has an actuator and a tissue retrieval bag. The actuator has a first end, a second end opposite the first end, a band segment extending from the second end towards the first end, and a foldable segment between the second end and the first end. The tissue retrieval bag has an open end, a closed end, and a cuff defining a passage extending peripherally around the open end. At least a portion of the band segment of the actuator is disposed in the passage. The actuator is foldable about the foldable segment between the insertion configuration of the tissue retrieval system in which the band segment and the tissue retrieval bag extend from the foldable segment towards the first end of the actuator and a deployment configuration of the tissue retrieval system in which the band segment and the tissue retrieval bag extend from the foldable segment away from the first end of the actuator.

DETAILED DESCRIPTION OF THE INVENTION

The tissue retrieval systems 10 described herein can provide an easy to use and cost effective system that effectively contains excised tissue specimens to prevent loss or spillage of tissue specimens into a body cavity. Furthermore, the tissue retrieval systems 10 can protect the body wall access port site from contamination with the excised tissue specimens during withdrawal of the tissue specimens from within the body cavity.

Figure 1:
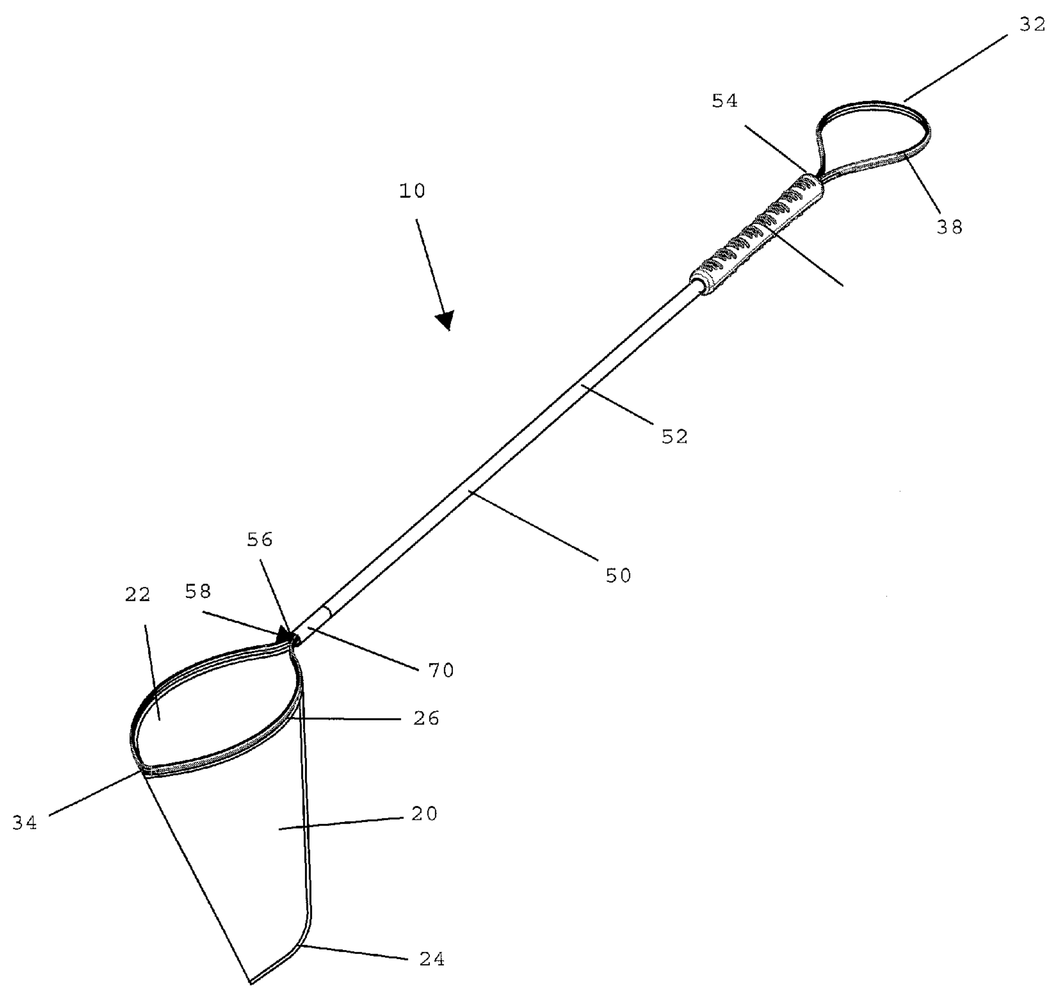
FIG. 1 is a perspective view of an embodiment of tissue retrieval system.
Figure 2:
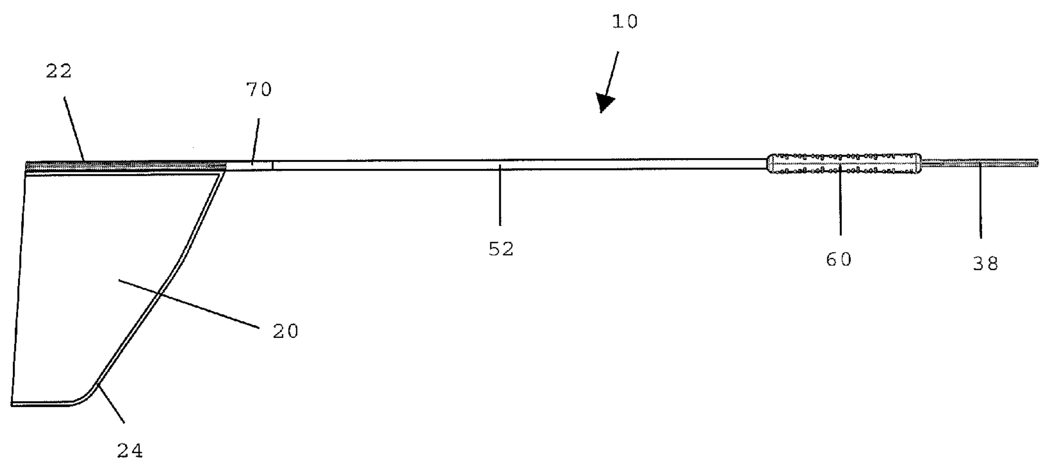
FIG. 2 is a side view of the tissue retrieval system of FIG. 1.
Figure 3:
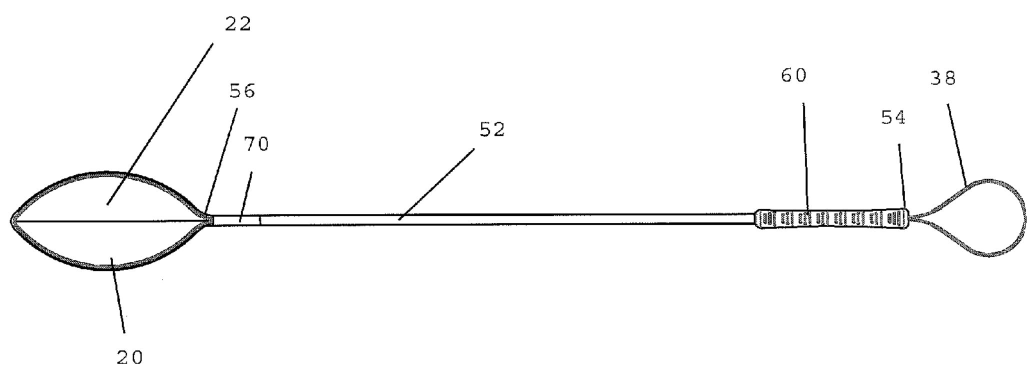
FIG. 3 is a top view of the tissue retrieval system of FIG. 1.

With reference to FIGS. 1-3, an embodiment of laparoscopic tissue retrieval system is illustrated. In various embodiments, the tissue retrieval system 10 can contain and withdraw excised tissue specimens from within a body cavity. After insertion of the tissue specimens into a retrieval bag 20 or pouch of the tissue retrieval system 10, the retrieval bag is then cinched closed to prevent spillage of its contents and to prevent contamination of the body cavity and body cavity wall during withdrawal of the retrieval bag from within the body cavity.

With continued reference to FIGS. 1-3, in some embodiments, the tissue retrieval system 10 comprises a tissue retrieval bag 20, an actuator 30, and an introducer 50. In certain embodiments, the tissue retrieval system 10 can further comprise a grip section 60. In certain embodiments, the tissue retrieval system 10 can further comprise a segment of shrink tubing 70.

With continued reference to FIGS. 1-3, the tissue retrieval bag 20 can be formed of a polymeric film material. For example, in some embodiments, the tissue retrieval bag 20 comprises a polyurethane film material. In other embodiments, the tissue retrieval bag can be formed of one or a combination of a variety of materials including polyurethane, polyethylene, polyimide, ripstop Nylon®, polyester, and Mylar®. Moreover, in certain embodiments, the tissue retrieval bag can be formed from laminated materials such as polyurethane coated ripstop Nylon, silicone coated ripstop Nylon, polyurethane coated ripstop polyester, silicone coated ripstop polyester, polyurethane coated taffeta, polyurethane coated spandex, or another suitable laminate.

In some embodiments, the retrieval bag 20 can be formed with two different thicknesses of the same film material. In these embodiments, the distal end, closed end, or tip portion of the retrieval bag would be formed with a thick film while the remainder of the retrieval bag would be formed with a thinner film. By incorporating a film with an increased thickness in the tip of the retrieval bag, the tensile and burst strengths of the retrieval bag can be increased. Furthermore, in certain embodiments, the tissue retrieval bag 20 can be formed with two different film materials. In this case, the tip of the retrieval bag would be formed from one material while the remainder of the retrieval bag would be formed from a different material. For example, the tip of the retrieval bag can be formed from a polyurethane and ripstop Nylon laminate while the remainder of the retrieval bag can be formed from a polyurethane film. The material utilized for the tip of the retrieval bag can have an increased thickness as compared to the material utilized for the remainder of the retrieval bag.

The tissue retrieval bag 20 can have an open end 22, a closed end 24, and a cuff 26 extending peripherally about the open end 22. In some embodiments, the retrieval bag 20 can be formed by welding a sheet of polymeric film material to form the closed end 24 while leaving an open end 22 unwelded. In other embodiments, other techniques of joining the material of the tissue retrieval bag 20 can be used to form the closed end 24. For example, in some embodiments, chemical adhesives can be used to form the closed end 24.

In some embodiments, the cuff 26 can be formed by welding or otherwise joining a portion of the material of the tissue retrieval bag 20 adjacent the open end 22 to itself to create a cuff 26 extending peripherally around the open end 22. The cuff 26 can have a passage extending therethrough.

With reference to FIGS. 1-3 and 10, the tissue retrieval system 10 comprises an actuator 30. The actuator 30 has a first end 32 and a second end 34 opposite the first end 32. The actuator 30 extends generally longitudinally between the first end 32 and the second end 34, defining a longitudinal axis A of the actuator. In the illustrated embodiment, the actuator 30 comprises a loop 40 or hoop segment at the second end 34. The loop 40 can be formed of a segment of flexible band 42. The flexible band 42 can have a generally rectangular cross-sectional profile with a height that is relatively large compared with a width of the band 42. Advantageously, this rectangular cross-sectional profile can provide flexural strength to support the tissue retrieval bag 20. In other embodiments, other cross-sectional profiles can be used. It can be desirable that these cross-sectional profiles include a relatively high height compared with a width. For example, in some embodiments, an oval cross-section can be used.

With reference to FIGS. 1-3 and 10, as illustrated, the tissue retrieval bag 20 is disposed on the loop 40 of the actuator 30. In some embodiments, the tissue retrieval system 10 can be assembled by: positioning the tissue retrieval bag 20 with its open end 22 adjacent the loop 40 of actuator 30; folding a portion of material of the tissue retrieval bag 20 at the open end 22 over the loop 40; and welding the portion of material of the tissue retrieval bag 20 that is folded over the loop 40 to the tissue retrieval bag 20. Desirably, the loop 40 of the actuator 30 for the retrieval bag is sized to be joined to the cuff 26 portion of the retrieval bag 20 in such a fold over and join technique to position the loop within the cuff of the retrieval bag.

With continued reference to FIGS. 1-3 and 10, as illustrated, the actuator 30 comprises at least one elongate arm such as a generally cylindrical segment 36 positioned between the first end 32 and the second end 34. In the illustrated embodiment, the actuator 30 comprises two elongate arms illustrated as generally cylindrical segments 36 joined by a flexible region such as a relatively lower diameter neck 37 extending therebetween. In other embodiments, the actuator 30 can comprise more or fewer than two generally cylindrical segments 36 such as, for example a single generally cylindrical segment or three or more generally cylindrical segments joined by a corresponding number of flexible regions or necks. In some embodiments, the at least one generally cylindrical segment 36 can comprise a solid rod. In other embodiments, the at least one generally cylindrical segment 36 can comprise a tubular member having a lumen extending longitudinally therethrough. While it can be desirable for sealing performance with a septum or other instrument seal that the elongate arm comprise at least one cylindrical segment 36, in some embodiments, the at least one elongate arm can comprise a non-cylindrical segment such as, for example an elongate arm having a generally rectangular, triangular, oval, elliptical, or other geometric cross-sectional profile.

Figure 9:
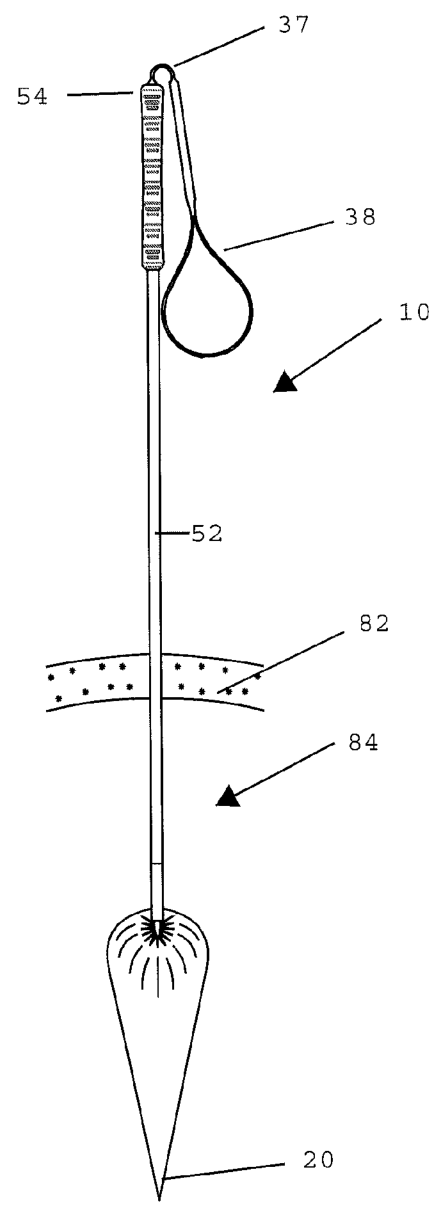
FIG. 9 is a top view of the tissue retrieval system of FIG. 1 at a surgical site with an insertion trocar withdrawn from the surgical site and with a handle of an actuator of the tissue retrieval system in a folded state.
Figure 10:
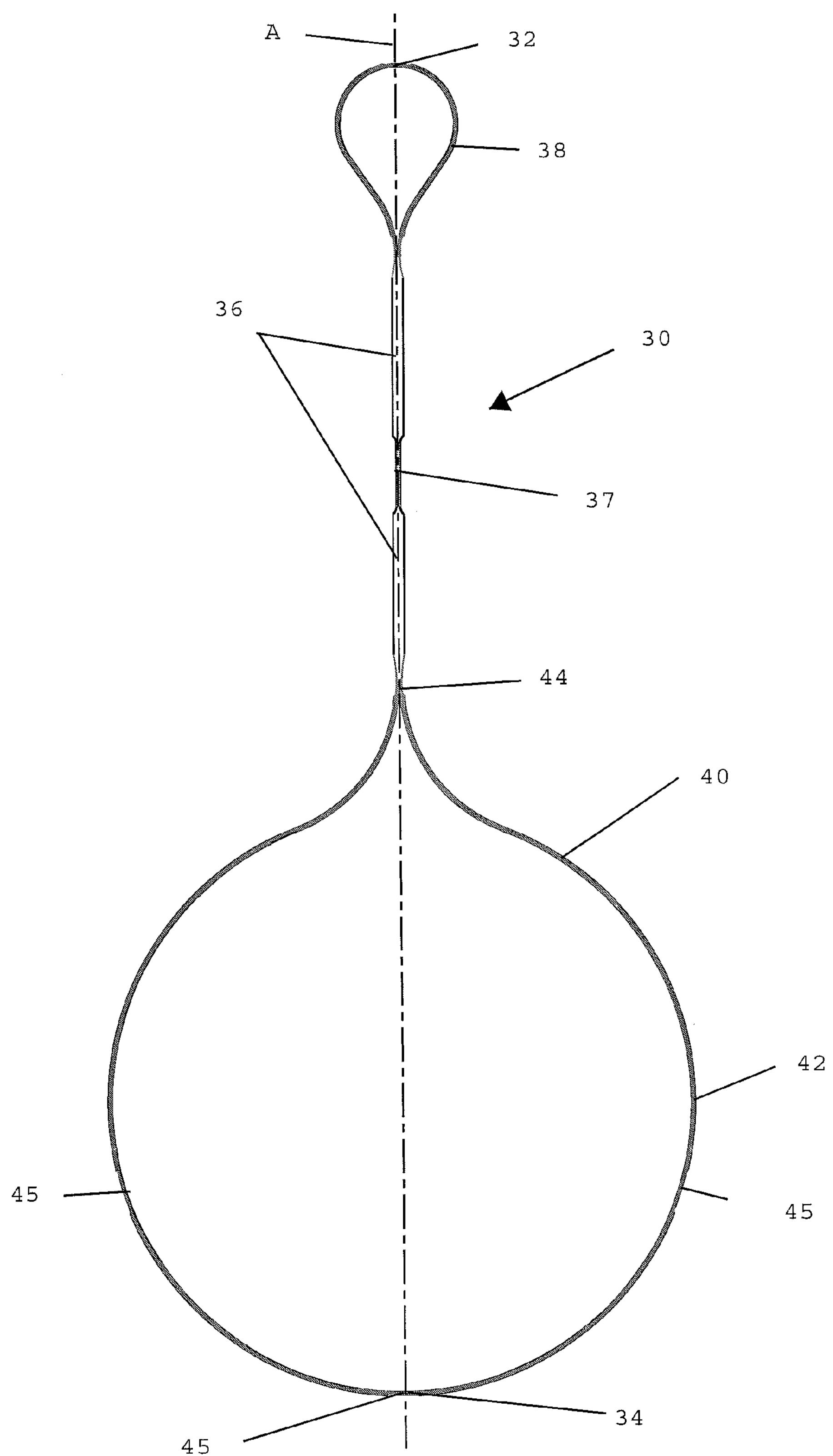
FIG. 10 is a top view of an actuator of the tissue retrieval system of FIG. 1.

With reference to FIG. 10, in the illustrated embodiment of actuator 30, the loop 40 is joined to a generally cylindrical segment 36, at a flexible or foldable segment 44. The flexible or foldable segment 44 can be formed by a localized relatively thin segment of the loop 40. In some embodiments the foldable segment 44 can be disposed on the loop 40 adjacent where the loop 40 joins the generally cylindrical segment 36. As further described herein, during insertion the tissue retrieval system 10 through an access device, such as a trocar, the loop 40 of the actuator 30 can be folded towards the first end 32 of the actuator at the foldable segment 44 to configure the tissue retrieval system 10 in an insertion configuration. In some embodiments, the loop 40 can comprise one or more hinge sections 45 having a relatively high flexibility to facilitate folding the loop 40 into the insertion configuration. In some embodiments, the hinge section 45 can be formed by a localized relatively thin segment of flexible band 42 material. In some embodiments, the loop 40 can include a hinged section 45 at a distal end thereof to allow the loop to be easily deformed from a generally circular profile to an almond-shaped or oval profile about the hinged section 45. In other embodiments, the loop 40 can comprise several hinged sections 45 peripherally spaced about the loop 40 to provide a desired flexibility. Advantageously, this foldability to an insertion configuration facilitates use of the tissue retrieval system 10 in a surgical procedure as described in further detail with reference to FIGS. 4-9.

With reference to FIGS. 1-3 and 10, in the illustrated embodiment, the actuator 30 comprises a handle segment 38 at the first end 32. In some embodiments, the handle segment 38 can comprise a flexible band formed to a loop configuration. As with the loop 40 at the second end 34 of the actuator 30, the flexible band of handle segment 38 can have a cross-sectional profile shaped and configured to provide a desired amount of flexural strength. For example, in some embodiments, the flexible band of the handle segment 38 has a substantially rectangular cross-section with a height relatively large compared to its width. In some embodiments, the actuator 30 does not comprise a handle segment. Rather, the elongate arm such as a generally cylindrical segment 36 can define the first end of the device.

In some embodiments, the actuator 30 can be formed of a unitary, monolithic construction. For example, the actuator 30 can be formed by a molding operation. Accordingly, in the illustrated embodiments, the actuator 30 is desirably formed of a flexible, moldable material. In some embodiments, the actuator 30 comprises a NYLON® material. Advantageously, a molded, monolithic actuator 30 can be manufactured quickly and at relatively low-cost. In other embodiments, the actuator can be formed of separate components that are welded, bonded, or otherwise joined to each other. For example, the flexible band of handle 38 and the loop 40 can be formed by extrusion and joined to a generally cylindrical segment 36 such as a tube or solid rod formed by molding. In some embodiments, the actuator could also be formed from an extruded strip and fastened together to create the loop and the handle. In these embodiments, the strip could be fastened by a variety of techniques, including heat staking, ultrasonic welding, adhesive bonding, and mechanical fastening.

In some embodiments, the handle 38 and/or the loop 40 can be welded, bonded, or otherwise joined to an outer surface of the generally cylindrical segment 36. In other embodiments, the generally cylindrical segment 36 can comprise a tubular member having a lumen therein. The handle 38 and/or the loop 40 can be welded, bonded, snap fit, or otherwise joined to the generally cylindrical segment 36 within the lumen. In these embodiments, once the handle 38 and/or the loop 40 are joined to the generally cylindrical segment 36, longitudinal movement of the handle 38 and/or the loop 40 relative to the generally cylindrical segment 36 is prevented. In certain embodiments, the handle can comprise a cord that is joined to a molded actuator by one of a variety of techniques. Moreover, in other embodiments, the actuator can be formed of a cord, or flexible braided tubing. In some embodiments, a polymer tube could also be used in place of the actuator.

With reference to FIGS. 1-3, the introducer 50 of the tissue retrieval system 10 comprises a tubular introducer member 52. The tubular introducer member 52 can extend generally longitudinally between a first end 54 and a second end 56. The tubular introducer member 52 can have a lumen 58 extending from the first end 54 to the second end 56. The introducer 50 can also include a grip 60 positioned about the tubular introducer member 52 adjacent the first end 54. In some embodiments, the grip 60 can be positioned elsewhere on the tubular introducer member 52.

While the illustrated embodiment includes an introducer 50 with a tubular member having a relatively constant outer diameter along its length, in other embodiments, introducer tube could have a small diameter section at the second end relative to the first end. In these embodiments, the small diameter section can correspond with the width of the retrieval bag 20 such that the retrieval bag could nest in the small diameter section of the introducer tube during insertion through a trocar to reduce the force required to advance the retrieval system through the trocar. The proximal portion of the introducer tube would have a larger diameter and would be sized to enable an access device such as a trocar to effectively maintain a seal around the introducer tube.

With reference to FIGS. 1-3 and 10, the actuator 30 is longitudinally slidably disposed within the lumen 58 of the introducer 50. Desirably, the generally cylindrical segment 36 of the actuator 30 is sized to sealingly engage an interior surface of the lumen 58 of the introducer 50. In some embodiments where the actuator includes an elongate arm that does not include a cylindrical segment, the introducer can have an interior geometry corresponding to that of the elongate arm such as, for example, a generally rectangular, triangular, oval, elliptical, or other geometric cross-sectional profile. Accordingly, the generally cylindrical segment 36 of the actuator can prevent loss of pneumoperitoneum through the introducer during a laparoscopic surgical procedure. In other embodiments, it can be desirable that a tissue retrieval system comprise a foldable actuator 30 without a corresponding introducer 50. Accordingly, advantageously, further manufacturing efficiencies and cost reduction can be achieved with a tissue retrieval system without an introducer 50.

In some embodiments, the tubular introducer member 52 can comprise a length of tubular material. For example, in certain embodiments, the tubular introducer member 52 can comprise an ABS extruded tube. In other embodiments, other suitable materials and manufacturing processes can be used to form the tubular introducer member. In some embodiments, the grip 60 can be formed of elastomeric material. For example, in some embodiments the grip 60 can comprise a KRATON® material.

With reference to FIGS. 1-3, the tissue retrieval system 10 can include a coupler, such as a segment of shrink tubing 70. The shrink tubing 70 can be positioned at the second end 56 of the introducer 50. In use, the shrink tubing 70 can maintain the position of the retrieval bag 20 and prevent migration of the retrieval bag 20 relative to the second end 56 of the tubular introducer member 52 and the loop 40 of the actuator 30 during insertion of the tissue retrieval system 10 through an access device. The coupler can also maintain the position of the retrieval bag 20 such that it can be cinched shut by sliding of the actuator 30 relative to the introducer 50. In some embodiments, the shrink tubing 70 can comprise a polyolefin material. In other embodiments, other suitable materials can be used.

In some embodiments, the tissue retrieval systems described herein can be sized and configured for application through a 10 mm trocar. Thus, an exterior surface of the introducer tubular member 52 can be sized to enable trocar seals of a 10 mm trocar to effectively maintain a seal around the introducer tubular member 52 to prevent loss of pneumoperitoneum during use of the device. Additionally, the combined diameters of an exterior surface of the introducer tubular member 52 having the tissue retrieval bag 20 adjacent in a folded, insertion configuration can be sized to pass through a 10 mm trocar. If it is desired that the retrieval bag 20 be inserted in an open, but unfolded configuration, in some embodiments, the combined diameters of an exterior surface of the introducer tubular member 52 and a grasper or other insertion tool can be sized to pass through a 10 mm trocar. In other embodiments, the tissue retrieval systems described herein can be sized and configured for application through a trocar having a size smaller or greater than 10 mm. For example, in some embodiments, the tissue retrieval system 10 can be sized to sized to fit through a 12 mm or 15 mm trocar. In these embodiments, the tissue retrieval system can have a retrieval bag with a larger volume than that of the retrieval system 10 sized for a 10 mm trocar. In other embodiments, the tissue retrieval system could be provided with a more elongated retrieval bag and sized to fit through a 5 mm or 8 mm trocar. In these embodiments, the introducer can have a small diameter section at the second end to allow the retrieval bag to nest into, thereby facilitating passage of the retrieval system through a 5 mm or 8 mm trocar. The proximal portion of the introducer tube would have a larger diameter to enable the trocar seal to effectively maintain a seal around the introducer tube A streamlined and relatively low cost method of assembling the tissue retrieval system 10 can be performed. In the method, an actuator 30 having a loop 40 is formed in a molding operation. A sheet of retrieval bag 20 material can be folded over the actuator loop 40 to form a cuff 26. The cuff can then be joined to the tissue bag 20 such as by a welding operation to restrain the loop 40 within the cuff 26 of the retrieval bag. The retrieval bag 20 material can then be folded and joined such as by welding to form a closed end. The shrink tubing 70 can be loosely placed over the introducer tubular member 52. The elastomeric grip 60 can be placed over the end of the introducer tubular member 52 opposite the shrink tubing 70. The elastomeric grip 60 can be secured in place via an interference fit with the introducer tubular member 52, or in some embodiments, can be adhered or otherwise joined to the introducer tubular member 52. The handle segment 38 on the actuator can then be folded to a flattened state and advanced through the second end 56 of the introducer tubular member 52 until the handle segment 38 extends beyond the first 54 end of the introducer tubular member 52. With the actuator 30 and retrieval bag 20 assembly positioned within the introducer 50, a portion of the retrieval bag 20 can be placed over the second end 56 of the introducer tubular member 52 and the shrink tubing 70 can be positioned over the retrieval bag 20. With the shrink tubing 70 positioned over the retrieval bag 20, the shrink tubing 70 can be heated to shrink the tubing and couple the retrieval bag to the outside of the introducer tube.

Figure 4:
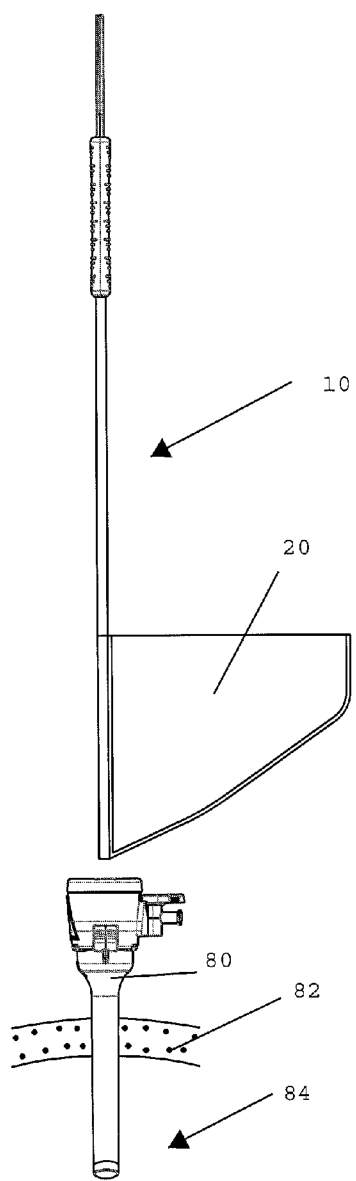
FIG. 4 is a side view of the tissue retrieval system of FIG. 1 positioned for insertion to a surgical site through a trocar.

With reference to FIGS. 4-9, a method of using the tissue retrieval systems 10 described herein through an access device such as a trocar 80 is illustrated. An access device is positioned through a body wall 82 to access a surgical site 84 using laparoscopic surgical techniques. With reference to FIG. 4, a tissue retrieval system 10 is first positioned exterior to the body wall 82 outside access device 80.

Figure 5:
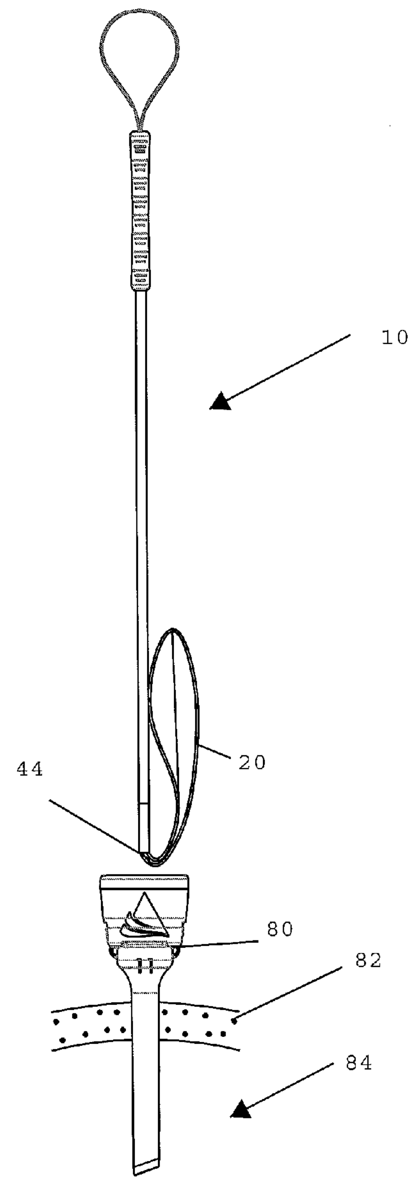
FIG. 5 is a top view of the tissue retrieval system of FIG. 1 in an insertion configuration for insertion to a surgical site through a trocar.

With reference to FIG. 5, the tissue retrieval system 10 can be manipulated to an insertion configuration. For example, as described above, the flexible band 42 of the loop 40 of the actuator has flexural strength to support the retrieval bag 20 and 10 serves to expand the retrieval bag 20 opening to facilitate the insertion of tissue specimens therein. However, the flexibility of the band 42 can allow the loop 40 of the actuator 30 to be folded about the foldable segment 44 and hinge segments 45 such that the loop 40 and the retrieval bag 20 extend along the actuator 30 towards the first end 32 of the actuator. Accordingly, with the tissue retrieval system 10 in the insertion configuration, the folded loop 40 can be aligned with a longitudinal axis of the introducer tubular member 52.

Figure 6:
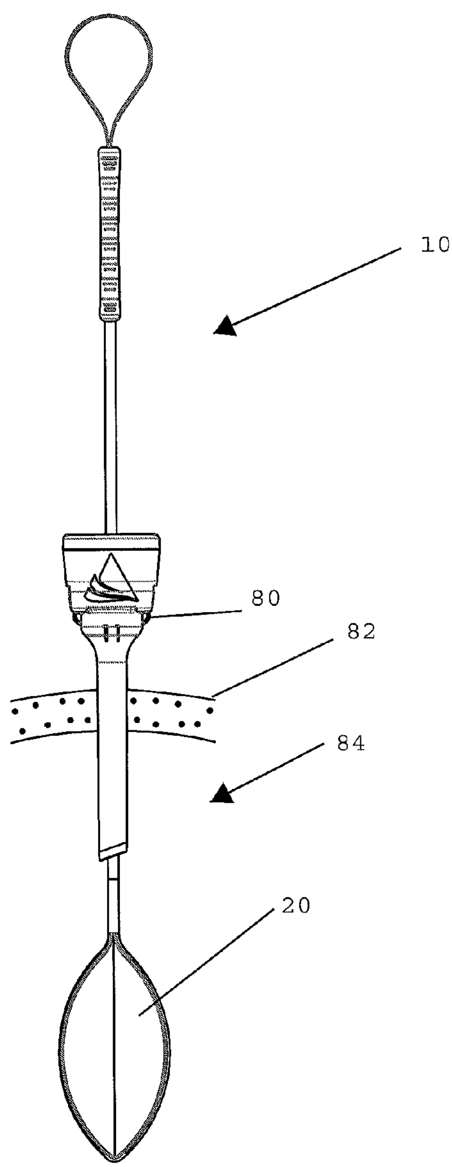
FIG. 6 is a top view of the tissue retrieval system of FIG. 1 as inserted through a trocar to a surgical site.

With reference to FIG. 6, the tissue retrieval system 10 in the insertion configuration (FIG. 5) can be advanced through the access device into the body cavity 84 until the retrieval bag 20 is extended beyond the distal end of the access device. The loop 40 of the actuator 30 then unfolds away from the introducer tubular member 52 into a deployed configuration defined by the bias of the flexible band 42. In the deployed configuration, a majority of the loop 40 is outside the introducer 50 to position the retrieval bag 20 in an expanded open configuration within the body cavity 84. One or more tissue specimens can then be loaded into the retrieval bag 20.

Figure 7:
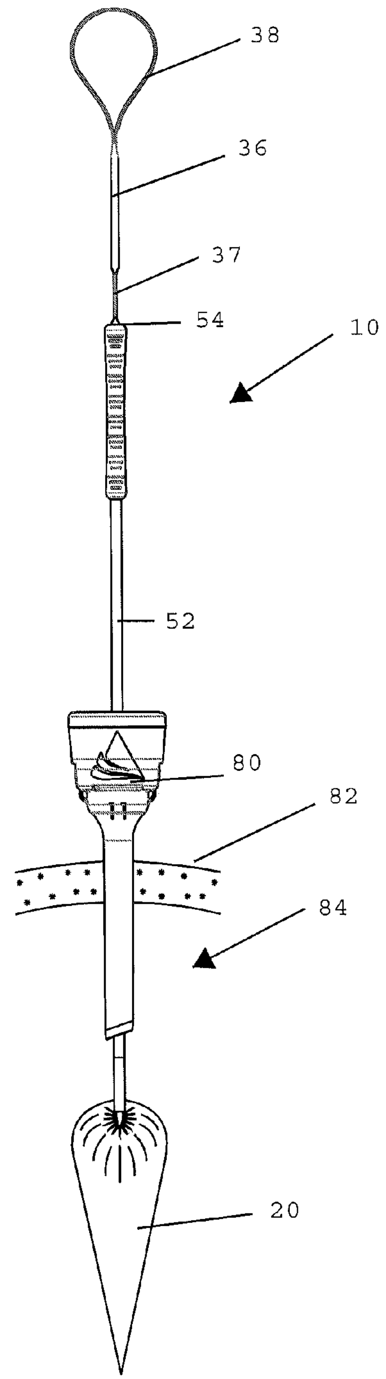
FIG. 7 is a top view of the tissue retrieval system of FIG. 1 as inserted through a trocar to a surgical site with an actuator of the tissue retrieval system withdrawn and a tissue retrieval bag in a cinched state.

With reference to FIG. 7, the tissue bag 20 can be cinched closed by withdrawing the actuator handle 38 relative to the introducer 50. As the handle is retracted, a majority of the loop 40 is pulled into the lumen of the introducer tubular member 52 until the open end 22 of the retrieval bag 20 is cinched closed by longitudinal sliding of the loop 40 relative to the cuff 26. The coupling of the retrieval bag 20 to the introducer 50 can provide resistance to cinch the tissue bag 20. In some embodiments, the actuator 30 can comprise a bead slidably disposed on the loop 40. In these embodiments, the actuator and loop can remain stationary and the bead can be longitudinally slid with a grasper or other instrument to cinch the bag closed. In embodiments of tissue retrieval system without an introducer 50, the bag can be left open and the open end withdrawn from the body cavity by withdrawing the elongate arm.

Figure 8:
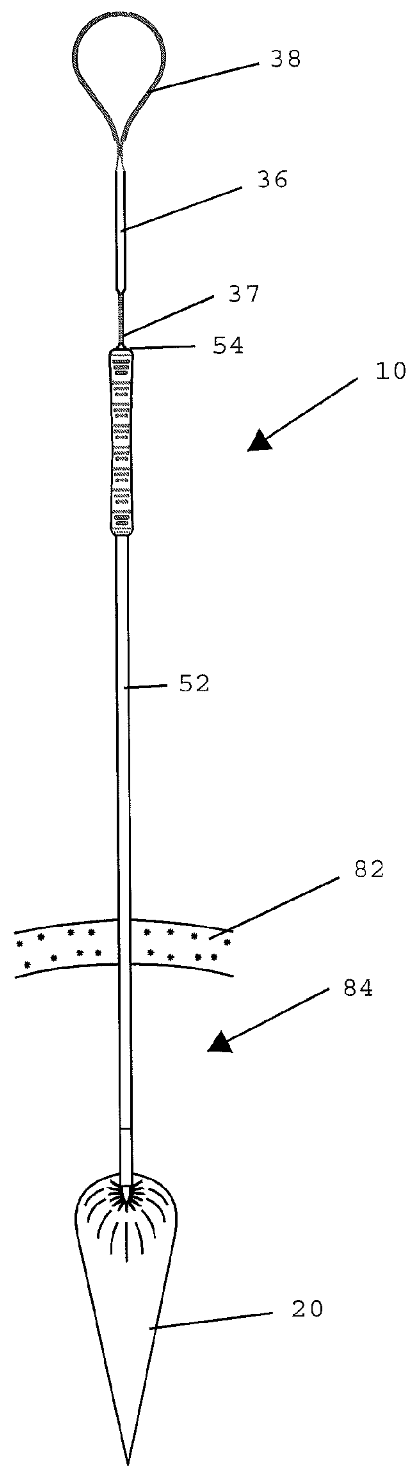
FIG. 8 is a top view of the tissue retrieval system of FIG. 1 at a surgical site with an insertion trocar withdrawn from the surgical site.

With reference to FIG. 8, the introducer tubular member 52 and the handle 38 of the retrieval system can be configured such that a 10 mm or larger trocar can be withdrawn over the first end 32 of the introducer tubular member 52 and the handle 38. Accordingly, in some embodiments, the trocar 80 can be removed from the surgical site while leaving the retrieval system 10 disposed in the body cavity 84 and across the body wall 82.

With reference to FIG. 9, once the trocar 80 is removed from the surgical site, the retrieval system 10 can then be withdrawn from the body cavity 84 and the body wall 82. Upon cinching of the retrieval bag 20, a neck 37 section of the actuator can be exposed beyond the first end 54 of the introducer tubular member 52. The neck 37 section serves as a hinge area and allows the actuator handle 38 to be folded toward the second end 34 of the actuator 30 at the actuator 30 and introducer 50 interface into a folded configuration such that the folded handle 38 is aligned with the axis of the introducer 50. Advantageously, the foldable handle 38 enables the handle 38 and the introducer 50 to be simultaneously grasped to facilitate withdrawal of the retrieval bag from the body cavity and the body wall. Furthermore, folding the handle 38 forward along the introducer 50 reduces the span from the retrieval bag 20 to the handle 38 and facilitates the withdrawal of the retrieval bag 20 from the patient.

In certain methods of use, the retrieval bag 20 can be partially withdrawn from the body wall and then re-opened by sliding the introducer 50 relative to the actuator 30. This reopening enables access to the retrieval bag 20 for removal of some of the contents to reduce the volume of the retrieval bag 20, thus facilitating withdrawal of the retrieval bag 20 through the body wall 82. In some procedures, a surgeon can also avoid the need for extending the body wall incision by reducing the volume of the contents in the retrieval bag 20 prior to withdrawal through the body wall 82. Graspers, forceps or aspiration devices can be used to remove contents from the retrieval bag. After removal of some or all of the contents, the retrieval bag 20 can be cinched closed by retracting the actuator.

By providing the tissue retrieval system with a foldable actuator 30 described herein, tissue retrieval systems 10 can be inserted without the use of a separate grasper or applicator. Thus, advantageously, the tissue retrieval systems 10 can be relatively rapidly applied without risking damage to the tissue bag 20 from some types of grasper tip.

In some embodiments, tissue retrieval systems can be configured to be inserted without folding the actuator with the use of a separate grasper or insertion instrument. For example, a tissue retrieval system with a tissue retrieval bag in the open configuration can be advanced through an access port via a grasper. As described above, it is desirable that in such a configuration it can be desirable that the tissue retrieval system be sized and configured to be received in a trocar having a predetermined diameter. The tissue retrieval bag can then be cinched closed by withdrawing the actuator with respect to the introducer such that the coupling of the tissue retrieval bag to the introducer cinches the bag closed as described above. Accordingly, it is contemplated that in some embodiments a tissue retrieval system can comprise a non-foldable actuator slidable within an introducer to which the tissue retrieval bag is coupled as described above.

Although this application discloses certain preferred embodiments and examples, it will be understood by those skilled in the art that the present inventions extend beyond the specifically disclosed embodiments to other alternative embodiments and/or uses of the invention and obvious modifications and equivalents thereof. Further, the various features of these inventions can be used alone, or in combination with other features of these inventions other than as expressly described above. Thus, it is intended that the scope of the present inventions herein disclosed should not be limited by the particular disclosed embodiments described above, but should be determined only by a fair reading of the claims that follow.

What is claimed is:

1. A tissue retrieval system comprising:

a tissue retrieval bag having an open end, a closed end, and a cuff extending peripherally around at least a portion of the open end;

a tubular introducer having a proximal end, a distal end, and a lumen extending generally longitudinally therethrough between the proximal end and the distal end;

a foldable actuator slidable within the tubular introducer, the foldable actuator having a first end and a second end opposite the first end, the actuator comprising:

a handle disposed at the first end;

an elongate arm between the first end and the second end, the elongate arm defining a longitudinal axis of the actuator, the elongate arm having a foldable neck between the first end and the second end; and a hoop segment extending distally from the elongate arm to the second end, the hoop segment partially disposed within the cuff of the tissue retrieval bag, the hoop segment biased into an open state to open the open end of the tissue retrieval bag; and wherein the actuator is slidable between a distal position relative to the tubular introducer defining a deployed configuration in which a portion of the hoop segment extends distally from the distal end of the introducer and a proximal position relative to the tubular introducer in which the cuff of the tissue retrieval bag is cinched against the distal end of the tubular introducer and the foldable neck of the elongate arm is positioned proximal of the proximal end of the tubular introducer wherein with the actuator in the proximal position, the actuator is foldable at the foldable neck relative to the tubular introducer into a withdrawal condition such that the first end of the actuator and the handle extends towards the distal end of the introducer.

2. The tissue retrieval system of claim 1, wherein the actuator further comprises a flexible segment on the hoop segment positioned distally of the distal end of the tubular introducer with the actuator in the distal position, the flexible segment is foldable about an axis transverse to the longitudinal axis such that in a folded state the portion of the hoop segment and the tissue retrieval bag extend along the tubular introducer in a first direction towards the proximal end of the introducer.

3. The tissue retrieval system of claim 1, further comprising a grip positioned on an exterior surface of the introducer.

4. The tissue retrieval system of claim 3, wherein the grip comprises an elastomeric material.

5. The tissue retrieval system of claim 1, wherein the actuator is unitarily formed in a monolithic construction.

6. The tissue retrieval system of claim 1, wherein the handle comprises a flexible band formed to a loop configuration.

7. The tissue retrieval system of claim 1, wherein the hoop segment comprises at least one hinge section having a relatively high flexibility such that the hoop segment can be deformed from the open state to a generally oval profile.

8. The tissue retrieval system of claim 1, wherein the tissue retrieval bag is coupled to the distal end of the introducer to maintain a position of the tissue retrieval bag relative to the distal end of the introducer.

9. A tissue retrieval system comprising:

a tissue retrieval bag having an open end, a closed end, and a cuff extending peripherally around at least a portion of the open end;

a tubular introducer having a proximal end, a distal end, and a lumen extending generally longitudinally therethrough between the proximal end and the distal end;

an actuator slidable within the lumen of the tubular introducer, the actuator having a first end extending from the proximal end of the introducer and a second end extending from the distal end of the introducer, the actuator comprising:

a first elongate arm slidably positionable within the lumen of the introducer;

a second elongate arm slidably positioned in the lumen of the introducer;

a flexible region joining the first elongate arm to the second elongate arm; and a hoop segment extending distally from the second elongate arm at the second end, the hoop segment partially disposed within the cuff of the tissue retrieval bag, the hoop segment biased into an open state to open the open end of the tissue retrieval bag; and wherein the tissue retrieval bag is coupled to the distal end of the tubular introducer to maintain a position of the tissue retrieval bag relative to the introducer, and wherein the actuator is foldable to an insertion configuration, while within the tubular introducer, such that the hoop segment and the tissue retrieval bag extend along an outer surface of the introducer toward the proximal end of the tubular introducer.

10. The tissue retrieval system of claim 9, further comprising a coupler coupling the tissue retrieval bag to the distal end of the introducer.

11. The tissue retrieval system of claim 9, wherein the hoop segment comprises a flexible band having a generally rectangular cross-sectional profile.

12. The tissue retrieval system of claim 9, wherein the first elongate arm comprises a generally cylindrical segment.

13. The tissue retrieval system of claim 9, wherein the first elongate arm comprises a first generally cylindrical segment, the second elongate arm comprises a second generally cylindrical segment, and the flexible region comprises a neck extending between the first elongate arm and the second elongate arm.

14. The tissue retrieval system of claim 9, wherein the hoop segment comprises at least one hinge section having a relatively high flexibility such that the hoop segment can be deformed from the open state to the insertion configuration.

15. The tissue retrieval system of claim 9, wherein the actuator is sized to sealingly engage the lumen of the tubular introducer.

* * * * *